US006290976B1

(12) United States Patent
Messenger

(10) Patent No.: US 6,290,976 B1
(45) Date of Patent: Sep. 18, 2001

(54) FACIAL SKIN DERMABRASION CLEANSING AND CONDITIONING COMPOSITION

(76) Inventor: Donna Messenger, 888 Boulevard of the Arts #1803, Sarasota, FL (US) 34236

( * ) Notice: Subject to any disclaimer, the term of this patent is extended or adjusted under 35 U.S.C. 154(b) by 0 days.

(21) Appl. No.: 09/544,636

(22) Filed: Apr. 6, 2000

(51) Int. Cl.[7] .......... A61K 7/00
(52) U.S. Cl. .......... 424/401; 514/844; 514/846
(58) Field of Search .......... 424/401; 514/844, 514/846

(56) References Cited

U.S. PATENT DOCUMENTS

| | | | |
|---|---|---|---|
| 4,284,533 | 8/1981 | Imamura et al. | 252/542 |
| 4,957,747 | 9/1990 | Stiefel | 424/691 |
| 4,992,476 | 2/1991 | Geria | 514/782 |
| 5,360,824 | 11/1994 | Barker | 424/680 |
| 5,679,877 | 10/1997 | Erilli et al. | 510/218 |
| 5,753,245 * | 5/1998 | Fowler et al. | 424/401 |
| 5,800,446 | 9/1998 | Banuchi | 606/131 |
| 5,891,449 | 4/1999 | Daniel et al. | 424/40 |

* cited by examiner

*Primary Examiner*—Shelley A. Dodson
*Assistant Examiner*—Konata M. George
(74) *Attorney, Agent, or Firm*—Charles J. Prescott

(57) ABSTRACT

A facial skin cleansing and reconditioning composition. The composition generally includes a preselected corundum as a mildly skin abrasive powder which has been decontaminated by gamma ray sterilization rendering it microbally controlled. The abrasive particles are fused and of highly uniform size and shape, that shape being substantially free of ragged edges which could rip at the pores or tear the skin. The composition also includes an emollient, an emulsifier, a chelating agent, a preservative and a diluent.

7 Claims, No Drawings

FACIAL SKIN DERMABRASION CLEANSING AND CONDITIONING COMPOSITION

BACKGROUND OF THE INVENTION

1. Scope of Invention

This invention relates generally to skin cleaning and conditioning agents, and more particularly to an improved facial skin abrading, conditioning and moisturizing compound in paste or cream form.

2. Prior Art

One of the early methods of exfoliating the skin was the use of LAVA soap. Later, other ingredients were used such as almond scrubs, apricot kernal scrubs and diatimatious earth as being somewhat less abusive to the skin during exfoliation. Scrubbing the skin with these compounds would remove the top layers of dead skin, particularly facial skin, to make it look clearer and more youthful.

LOOFA sponges or a "buff puff" produce the same effect with somewhat better results, however. Following that improvement, a more recent method of exfoliation was introduced into a clinical or a beauty salon setting. This latest procedure, most popularly recognized under the term "Power Peel" or "Microdermabrasion" involves the utilization of a machine which shoots a blast of aluminum oxide onto the skin to create controlled skin injury producing an immediate body reaction to effect repair. As a result, healthy, plump skin cells are produced in a substantially shorter time than does the natural skin replacement cycle of 21 to 28 days. As the results of the Power Peel are cumulative, most technicians recommend five (5) to ten (10) treatments spaced apart a week or two, especially where brown spots, fine lines, stretch marks, chicken-pock marks and even tattoos are to be removed. However, the Power Peel is a very costly process and must be done in a clinical setting by trained technicians.

The use of conditioning creams and lotions to enhance the condition of human skin is also well known. More specifically, cleansing agents, emollients, emulsifiers and abrading agents are also well known for improving the condition of facial skin.

U.S. Pat. No. 5,891,449 invented by Daniel et al., teaches such a skin cleaning agent and method of use which includes surfactants, a washing agent, an abrasive, adjuvants for consistency, appearance, odor and stability. Stiefel, in U.S. Pat. No. 4,957,747 also teaches a method of treating aging skin which includes the use of a composition containing a suspension of fine particles of non-absorbable aluminum oxide abrasive in a topically acceptable aqueous base of sodium cocoisethionate, at least one emollient and a suspending agent.

In U.S. Pat. No. 5,679,877, Erilli et al. discloses a cleaning composition containing an abrasive along with paraffin sulfonate, an ethoxylated alkyl ether sulfate, essential oil and water. Another personal cleansing composition is disclosed by Fowler et al. in U.S. Pat. No. 5,753,245 which include insoluble micronized cleansing particles so minute as to be tacitly undetectable by the user during the cleansing process. A surfactant, an emollient and water are included in this composition.

A human skin cleansing and wrinkle-reducing cream invented by Barker is shown in U.S. Pat. No. 5,360,824. Disclosed therein is a cleansing cream which includes water soluble granules sufficient in size, quantity and hardness to abrade the keratinized outer epidermal layer of the skin. Included are water soluble vitamins and a base in which the granules are substantially uniformly disposed, preferably formed of oil and a petrolatum jelly.

Another skin cleansing and moisturizing composition is disclosed by Geria in U.S. Pat. No. 4,992,476 teaching a skin cleansing and moisturizing composition including an oil phase, an aqueous phase and an abrasive which removes oily deposits, cosmetics and particulates from the skin surface, but does not apparently abrade the facial skin itself.

Still another liquid abrasive-containing skin cleanser composition is disclosed in U.S. Pat. No. 4,284,533 invented by Imamura, et al. teaching a liquid cleanser composition including partially cross-linked polyacrylic acid, a hydrotrope, a non-ionic sulficant and a water insoluble abrasive.

Lastly, Banuchi, in U.S. Pat. No. 5,800,446, teaches a glove and an epidermal stick, each of which have skin abrading properties associated with distal portions thereof, which may be applied against the epidermal portion of the skin to effect dermabrading thereof.

The present invention provides a unique composition in paste or, preferably, cream form which affords the benefits of mild facial skin dermabrasion without ripping or tearing skin pores. Also included are selected emollients, emulsifiers, a moisturizer, a chelator and other preservatives to prolong the useful life of the composition and render it substantially non-degradating and antibacterial as quantities of the composition are finger removed from a container thereof. By using the present invention in manually scrubbing the facial skin in a circular motion for just a few minutes, almost the same level of injury to the facial skin caused by the Power Peel process is produced using the present invention. This facial skin dermabrasion speeds up the facial skin cell turnover which produces the healthier plumper facial skin cells in a short period of time.

BRIEF SUMMARY OF THE INVENTION

This invention is directed to a facial skin cleansing and reconditioning composition. The composition generally includes a preselected corundum as a mildly skin abrasive powder which has been decontaminated by gamma ray sterilization rendering it microbally controlled. The abrasive particles are fused and of highly uniform size and shape, that shape being substantially free of ragged or uneven edges which could rip at the pores or tear the skin. The composition also includes an emollient, an emulsifier, a chelating agent, a preservative and a diluent.

It is therefore an object of this invention to provide a manually applied facial skin mildly dermabrading, cleansing and conditioning composition which provides limiting, non-damaging dermabrasion when manually applied over the facial skin.

It is another object of this invention to provide a skin dermabrasion composition which includes additional ingredients for facial skin conditioning and enhancement during the manual dermabrasion process.

In accordance with these and other objects which will become apparent hereinafter, the instant invention will now be described with reference to the accompanying drawings.

DETAILED DESCRIPTION OF THE INVENTION

The present invention affords an improved compound for dermabrading, conditioning, rejuvenating and moisturizing facial skin. The form of this composition is either a cream or paste uniformly blended with all ingredients being substantially uniformly distributed therethrough.

A primary ingredient of this invention is an alpha alumina or corundum particle structure which possesses the facial skin dermabrading property which avoids the ripping of skin pores or the tearing of facial skin, unlike other products in prior art. This physical attribute is derived from use of a purer and more consistent sized form of corundum or alumina particles or powder which appears to eliminate substantial jagged edges of the particles or powder which are notoriously otherwise the cause of such facial skin abuse in prior art compounds. The uniform shape of each particle of corundum is sometimes referred to as that of a "block t" which is more uniform and less damaging to facial skin.

Corundum, or a aluminum oxide ($Al_2O_3$) is typically a white powder, insoluble in water with some levels of impurity called "emery". Its crystals are barrel-shaped prisms of the trigonal system. Poorer in quality, synthetic corundum is used in industry as a manufacturing abrasive. When pure, corundum is colorless and transparent and only exceeded in its hardness by diamonds.

The stable alpha alumina form makes up the corundum used in the present invention and has a purity level of at least about 99% and is substantially devoid of impurities such as those forming rubies and sapphires, rendering such impure aluminum oxide, sometimes called "emery", as being worthy of gemstone utilization, however.

The preferred source of corundum powder utilized in the present invention is available through Micro Abrasives Corp. in Westfield, Mass. under the trademark MICROGRIT. The "WA" grade, referring to white aluminum oxide grains, is of high purity. It is friable and is screened to precise standards. Corundum formed under fusion in this grade possesses particularly low levels of aggressive or jagged edges, in part, due to its well-developed hexagonal crystal structure. Additionally, by providing a very uniform average particle size in the range of preferably about 120 FEPA (Federal European Abrasive Producers) standard or about 125 microns, the individual particles have less opportunity to excessively abrade facial skin tissue. Additionally, the corundum is pretreated with, preferably, gamma radiation to destroy any microbs existing on or within the cavities of the corundum particles. The preferred quantity of corundum powder in the cream form of the admixture ranges from 30% to 60% by weight, with 40% being preferred.

The present invention includes several additional ingredients which enhance the overall effectiveness of the corundum and render it useful in facial skin dermabrasion and conditioning. One or more emollients are provided which relax and soften facial skin tissue. At least one emulsifier is also included to provide for maintaining the uniform dispersion of other ingredients in the paste or cream consistency of the invention. One or more preservatives are also included to prevent decontamination and loss of the intended microbe-free nature of the invention as it is used. Typically, the hands and fingers of the user dipping into and removing small quantities of the cream or paste will carry undesirable microbes into the remainder of the admixture, the preservatives intended to arrest any such microbe growth. The reminder of the admixture or compound of the present invention includes a dilutent, preferably water, added in amounts sufficient to achieve the desired paste or creamy textured consistency.

The ingredients utilized in the present invention in the form of an emollient are as follows:

Stearic Acid;

Mineral oil;

Cetyl Alcohol;

Glyceryl Stearate SE; and

Cocoa Butter (Theobroma Cacao)

One or more emulsifiers are selected from the following group:

Stearic Acid (as an emollient);

Cetyl Alcohol (also an emollient);

Glyceryl Stearate SE (also an emollient); and

Polysorbate 20

One or more Preservatives are selected from the following group of ingredients:

Sodium Benzoate;

Methylparaben;

Propylaraben;

Diazolidinyl Urea.

A separate chelator formed of trisodium EDTA (eithylenediaminetetrac acetic acid) is included in the preferred embodiment of the compound serving as both an additional preservative by scavenging ions and microbs which find their way into the compound remaining in the container after hand removal of small quantities thereof during use.

An additional ingredient in the form of titanium oxide is also preferred as providing UV ray protection for the treated, sensitive facial skin area.

The preferred form of the invention was prepared by Corwood Laboratories, Inc. of Hauppuge, N.Y. as follows:

EXAMPLE I

| Ingredients | Range % | Function |
|---|---|---|
| Water | QS to 100% | Diluent |
| Corundum | 40% | Abrasive |
| Stearic Acid | 6–8% | Emulsifier/Emollient |
| Mineral Oil | 56% | Emollient |
| Cetyl Alcohol | 2–3% | Emulsifier/Emollient |
| Glyceryl Stearate SE | 1–2% | Emulsifier/Emollient |
| Cocoa (Theobroma Cacao) Butter | 1% | Emollient/Fragrance |
| Polysorbate 20 | Less than 1% | Emulsifier |
| Titanium Dioxide | Less than 1% | Opacifier |
| Aloe Barbadensis (Aloe Vera) Gel | Less than 1% | Protectant/Moisturizer |
| Tocopheryl Acetate (Vitamin E) | Less than 1% | Vitamin/Antioxidant |
| Triethanolamine | Less than 1% | Neutralizer |
| Trisodium EDTA | 0.10% | Chelator |
| Sodium Benzoate | 0.10% | Preservative |
| Methylparaben | 0.25% | Preservative |
| Propylparaben | 0.10% | Preservative |
| Diazolidinyl Urea | 0.20% | Preservative |

In application, it is preferred that the present invention in cream form be applied manually by moving the fingers in a circular motion with the cream spread over the facial tissue for a period of one to three minutes. Thereafter, the residue may be easily washed away with clear water or a mild water/detergent combination if desired.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A facial skin cleansing and conditioning composition consisting essentially of:

a mild skin abrasive including corundum powder of substantially uniform size and shape having a purity of at least 99% and a size of about 120 FEPA;

an emulsifier including stearic acid, cetyl alcohol, and glyceryl sterate SE and polysorbate 20;

an emollient including mineral oil and cocoa butter (theobrama cacao);

a protectant and moisturizer including aloe vera (aloe barbadensis);

a neutralizer including triethanolamine;

a chelator including trisodium EDTA;

a preservative including methyl paraben, propylparaben and diasolidinyl urea; and a diluent.

2. A facial skin cleansing and conditioning composition consisting essentially of:

a mild skin abrasive including corundum powder of substantially uniform size and shape having a purity of at least 99% and a size of about 120 FEPA;

an emulsifier including stearic acid, cetyl alcohol, and glyceryl sterate SE and polysorbate 20;

an emollient including mineral oil and cocoa butter (theobrama cacao);

a protectant and moisturizer;

a neutralizer including triethanolamine;

a chelator including trisodium EDTA;

a preservative including methyl paraben, propylparaben and diasolidinyl urea; and a diluent.

3. A facial skin cleansing and conditioning composition consisting essentially of:

a mild skin abrasive including corundum powder of substantially uniform size and shape having a purity of at least 99% and a size of about 120 FEPA;

an emulsifier including stearic acid, cetyl alcohol, and glyceryl sterate SE and polysorbate 20;

an emollient including mineral oil and cocoa butter (theobrama cacao);

a protectant and moisturizer including aloe vera (aloe barbadensis);

a neutralizer including triethanolamine;

a chelator including trisodium EDTA;

a preservative including methyl paraben, propylparaben and diasolidinyl urea;

a diluent; and an antioxident including vitamin E.

4. A facial skin cleansing and conditioning composition consisting essentially of:

a mild skin abrasive including corundum powder of substantially uniform size and shape having a purity of at least 99% and a size of about 120 FEPA;

an emulsifier including stearic acid, cetyl alcohol, and glyceryl sterate SE;

an emollient including mineral oil and cocoa butter (theobrama cacao);

a protectant and moisturizer including aloe vera (aloe barbadensis);

a neutralizer including triethanolamine;

a chelator including trisodium EDTA;

a preservative including methyl paraben, propylparaben and diasolidinyl urea; and a diluent.

5. A facial skin cleansing and conditioning composition consisting essentially of:

a mild skin abrasive including corundum powder of substantially uniform size and shape having a purity of at least 99% and a size of about 120 FEPA;

an emulsifier including stearic acid, cetyl alcohol, and glyceryl sterate SE and polysorbate 20;

an emollient;

a protectant and moisturizer including aloe vera (aloe barbadensis);

a neutralizer including triethanolamine;

a chelator including trisodium EDTA;

a preservative including methyl paraben, propylparaben and diasolidinyl urea; and a diluent.

6. A facial skin cleansing and conditioning composition consisting essentially of:

a mild skin abrasive including corundum powder of substantially uniform size and shape having a purity of at least 99% and a size of about 120 FEPA;

an emulsifier including stearic acid, cetyl alcohol, and glyceryl sterate SE and polysorbate 20;

an emollient including mineral oil and cocoa butter (theobrama cacao);

a protectant and moisturizer including aloe vera (aloe barbadensis);

a neutralizer including triethanolamine;

a chelator including trisodium EDTA;

a preservative including methyl paraben and propylparaben; and a diluent.

7. A facial skin cleansing and conditioning composition consisting essentially of:

a mild skin abrasive including corundum powder of substantially uniform size and shape having a purity of at least 99% and a size of about 120 FEPA;

an emulsifier including stearic acid, cetyl alcohol, and glyceryl sterate SE;

an emollient;

a protectant and moisturizer;

a neutralizer including triethanolamine;

a chelator including trisodium EDTA;

a preservative including methyl paraben and propylparaben; and a diluent.

* * * * *

UNITED STATES PATENT AND TRADEMARK OFFICE
Certificate

Patent No. 6,290,976 B1 Patented: September 18, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Donna Messenger, Sarasota, FL (US); and Lynn Lucka, New York, NY (US).

Signed and Sealed this Seventh Day of August 2007.

WILLIAM R. DIXON, JR.
*Special Program Examiner*
Technology Center 1600

UNITED STATES PATENT AND TRADEMARK OFFICE

CERTIFICATE OF CORRECTION

PATENT NO. : 6,290,976 C1
APPLICATION NO. : 90/011145
DATED : July 17, 2012
INVENTOR(S) : Messenger et al.

It is certified that error appears in the above-identified patent and that said Letters Patent is hereby corrected as shown below:

Delete “neurtalizer” at column 1, line 54 and insert --neutralizer-- therefor.

Signed and Sealed this
Eighteenth Day of December, 2012

David J. Kappos
*Director of the United States Patent and Trademark Office*

US006290976C1

(12) EX PARTE REEXAMINATION CERTIFICATE (9136th)

United States Patent

Messenger et al.

(10) Number: US 6,290,976 C1

(45) Certificate Issued: Jul. 17, 2012

(54) FACIAL SKIN DERMABRASION CLEANSING AND CONDITIONING COMPOSITION

(75) Inventors: Donna Messenger, Sarasota, FL (US); Lynn Lucka, New York, NY (US)

(73) Assignee: Bella Bella, Inc., New York, NY (US)

Reexamination Request:
No. 90/011,145, Aug. 23, 2010

Reexamination Certificate for:

| | |
|---|---|
| Patent No.: | **6,290,976** |
| Issued: | **Sep. 18, 2001** |
| Appl. No.: | **09/544,636** |
| Filed: | **Apr. 6, 2000** |

Certificate of Correction issued Aug. 7, 2007.

(51) Int. Cl.

| | |
|---|---|
| ***A61K 8/26*** | (2006.01) |
| ***A61K 8/19*** | (2006.01) |
| ***A61Q 19/00*** | (2006.01) |

(52) U.S. Cl. ........................ 424/401; 514/844; 514/846

(58) Field of Classification Search ........................ None
See application file for complete search history.

(56) References Cited

To view the complete listing of prior art documents cited during the proceeding for Reexamination Control Number 90/011,145, please refer to the USPTO's public Patent Application Information Retrieval (PAIR) system under the Display References tab.

*Primary Examiner*—Gary Kunz

(57) ABSTRACT

A facial skin cleansing and reconditioning composition. The composition generally includes a preselected corundum as a mildly skin abrasive powder which has been decontaminated by gamma ray sterilization rendering it microbally controlled. The abrasive particles are fused and of highly uniform size and shape, that shape being substantially free of ragged edges which could rip at the pores or tear the skin. The composition also includes an emollient, an emulsifier, a chelating agent, a preservative and a diluent.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-7 is confirmed.

New claims 8-14 are added and determined to be patentable.

*8. A facial skin cleansing and conditioning composition consisting essentially of:*

*a mild skin abrasive including corundum powder of substantially uniform size and shape having a purity of at least 99% and a size of about 120 FEPA;*

*an emulsifier comprising one or more of the following: stearic acid, cetyl alcohol, glyceryl sterate SE and polysorbate 20;*

*an emollient comprising one or both of the following: mineral oil and cocoa butter (theobrama cacao);*

*a protectant and moisturizer including aloe vera (aloe barbadensis);*

*a neutralizer including triethanolamine;*

*a chelator including trisodium EDTA;*

*a preservative comprising one or more of the following: methyl paraben, propylparaben and diasolidinyl urea; and*

*a diluent.*

*9. A facial skin cleansing and conditioning composition consisting essentially of:*

*a mild skin abrasive including corundum powder of substantially uniform size and shape having a purity of at least 99% and a size of about 120 FEPA;*

*an emulsifier comprising one or more of the following: stearic acid, cetyl alcohol, glyceryl sterate SE and polysorbate 20;*

*an emollient comprising one or both of the following: mineral oil and cocoa butter (theobrama cacao);*

*a protectant and moisturizer;*

*a neurtalizer including triethanolamine;*

*a chelator including trisodium EDTA;*

*a preservative comprising one or more of the following: methyl paraben, propylparaben and diasolidinyl urea; and*

*a diluent.*

*10. A facial skin cleansing and conditioning composition consisting essentially of:*

*a mild skin abrasive including corundum powder of substantially uniform size and shape having a purity of at least 99% and a size of about 120 FEPA;*

*an emulsifier comprising one or more of the following: stearic acid, cetyl alcohol, glyceryl sterate SE and polysorbate 20;*

*an emollient comprising one or both of the following: mineral oil and cocoa butter (theobrama cacao);*

*a protectant and moisturizer including aloe vera (aloe barbadensis);*

*a neutralizer including triethanolamine;*

*a chelator including trisodium EDTA;*

*a preservative comprising one or more of the following: methyl paraben, propylparaben and diasolidinyl urea;*

*a diluent; and*

*an antioxident including vitamin E.*

*11. A facial skin cleansing and conditioning composition consisting essentially of:*

*a mild skin abrasive including corundum powder of substantially uniform size and shape having a purity of at least 99% and a size of about 120 FEPA;*

*an emulsifier comprising one or more of the following: stearic acid, cetyl alcohol, and glyceryl sterate SE;*

*an emollient comprising one or both of the following: mineral oil and cocoa butter (theobrama cacao);*

*a protectant and moisturizer including aloe vera (aloe barbedensis);*

*a neutralizer including triethanolamine;*

*a chelator including trisodium EDTA;*

*a preservative comprising one or more of the following: methyl paraben, propylparaben and diasolidinyl urea; and*

*a diluent.*

*12. A facial skin cleansing and conditioning composition consisting essentially of:*

*a mild skin abrasive including corundum powder of substantially uniform size and shape having a purity of at least 99% and a size of about 120 FEPA;*

*an emulsifier comprising one or more of the following: stearic acid, cetyl alcohol, glyceryl sterate SE and polysorbate 20;*

*an emollient;*

*a protectant and moisturizer including aloe vera (aloe barbadensis);*

*a neutralizer including triethanolamine;*

*a chelator including trisodium EDTA;*

*a preservative comprising one or more of the following: methyl paraben, propylparaben and diasolidinyl urea; and*

*a diluent.*

*13. A facial skin cleansing and conditioning composition consisting essentially of:*

*a mild skin abrasive including corundum powder of substantially uniform size and shape having a purity of at least 99% and a size of about 120 FEPA;*

*an emulsifier comprising one or more of the following: stearic acid, cetyl alcohol, glyceryl sterate SE and polysorbate 20;*

*an emollient comprising one or both of the following: mineral oil and cocoa butter (theobrama cacao);*

*a protectant and moisturizer including aloe vera (aloe barbadensis);*

*a neutralizer including triethanolamine;*

*a chelator including trisodium EDTA;*

*a preservative comprising one or both of the following: methyl paraben and propylparaben; and*

*a diluent.*

*14. A facial skin cleansing and conditioning composition consisting essentially of:*

*a mild skin abrasive including corundum powder of substantially uniform size and shape having a purity of at least 99% and a size of about 120 FEPA;*

*an emulsifier comprising one or more of the following: stearic acid, cetyl alcohol, and glyceryl sterate SE;*

*an emollient;*

*a protectant and moisturizer;*

*a neutralizer including triethanolamine;*

*a chelator including trisodium EDTA;*

*a preservative comprising one or both of the following: methyl paraben and propylparaben; and*

*a diluent.*

* * * * *